(12) United States Patent
Wang et al.

(10) Patent No.: US 7,622,586 B2
(45) Date of Patent: Nov. 24, 2009

(54) OPIATE INTERMEDIATES AND METHODS OF SYNTHESIS

(75) Inventors: Peter Xianqi Wang, Chesterfield, MO (US); Frank W. Moser, Arnold, MO (US); Gary L. Cantrell, Troy, IL (US)

(73) Assignee: Mallinckrodt Inc., Hazelwood, MO (US)

( * ) Notice: Subject to any disclaimer, the term of this patent is extended or adjusted under 35 U.S.C. 154(b) by 213 days.

(21) Appl. No.: 11/741,932

(22) Filed: Apr. 30, 2007

(65) Prior Publication Data

US 2007/0244327 A1    Oct. 18, 2007

(51) Int. Cl.
*C07D 217/20*    (2006.01)
(52) U.S. Cl. ..................................... 546/149
(58) Field of Classification Search .................. None
See application file for complete search history.

(56) References Cited

U.S. PATENT DOCUMENTS

| | | |
|---|---|---|
| 3,168,546 A | 2/1965 | Ballauf et al. |
| 3,438,989 A | 4/1969 | Shavel Jr. et al. |
| 3,652,633 A | 3/1972 | Distler et al. |
| 3,862,327 A | 1/1975 | Covey et al. |
| 3,914,233 A | 10/1975 | Mohacsi et al. |
| 3,922,285 A | 11/1975 | Leimgruber et al. |
| 4,368,326 A | 1/1983 | Rice |
| 4,384,991 A | 5/1983 | Balazs et al. |
| 4,410,700 A | 10/1983 | Rice |
| 4,452,601 A | 6/1984 | Collins et al. |
| 4,514,569 A | 4/1985 | Hendrickson et al. |
| 4,521,601 A | 6/1985 | Rice |
| 4,613,668 A | 9/1986 | Rice et al. |
| 4,727,146 A | 2/1988 | Rice |
| 4,737,504 A | 4/1988 | Miller et al. |
| 5,023,342 A | 6/1991 | Sharpless et al. |
| 5,286,899 A | 2/1994 | Gao |
| 5,445,164 A | 8/1995 | Worthen et al. |
| 5,446,164 A | 8/1995 | Ishikawa et al. |
| 5,519,034 A | 5/1996 | Kozlik et al. |
| 5,668,285 A | 9/1997 | Rice et al. |
| 5,804,586 A | 9/1998 | Sargent et al. |
| 5,807,868 A | 9/1998 | Sargent et al. |
| 5,869,697 A | 2/1999 | Busheam et al. |
| 6,043,253 A | 3/2000 | Brockunier et al. |
| 6,566,525 B1 | 5/2003 | Kim et al. |
| 6,593,341 B2 | 7/2003 | Feller et al. |
| 6,596,734 B1 | 7/2003 | Feller et al. |
| 2003/0073742 A1 | 4/2003 | Thijs et al. |
| 2003/0176414 A1 | 9/2003 | Guarna et al. |

FOREIGN PATENT DOCUMENTS

| | | |
|---|---|---|
| DE | 1138765 | 10/1962 |
| GB | 685748 | 1/1953 |
| WO | WO 82/04049 | 11/1992 |

OTHER PUBLICATIONS

Hong et al., Preparation of Opium Alkaloids by Palladium Catalyzed Bis-Cyclizaions. Formal Total Synthesis of Morphine., Tetrahedron Letters, vol. 35, No. 21, pp. 3453-3456, 1994, XP-002376506 (Search Report Apr. 11, 2006).

Hsu, et al., 215. Total Synthesis of (±)-3-Deoxy-7,8-dihydromorphine, Helvetica Chimica Acta, vol. 63, Fasc. 7, 1980-Nr. 215, pp. 2042-2045.

Degraw et al.; Investigation of the Grewe Codeine Method. Attempts to Achieve a Practical Synthesis, J. Heterocyclic Chem., vol. II, Jun. 1974, pp. 363-367.

Beyerman et al., Lab. Org. Chem., Tech. Hogesch. Delft. Delft. Neth.); Recl. Trav. Chim. Pays-Bas, 1976, 95(7-8), 184-8 (Eng.), pp. 182-187.

Seyden-Penne, Chiral Auxilianies and Ligands in Asymmetric Synthesis, 1995, pp. 230-240.

*Primary Examiner*—Zinna N Davis

(57) ABSTRACT

Novel opiate intermediate compositions and methods of synthesis that include changing the substitution pattern on the aromatic ring of the pre-Grewe intermediate are provided.

3 Claims, No Drawings

OPIATE INTERMEDIATES AND METHODS OF SYNTHESIS

CROSS REFERENCE TO RELATED APPLICATIONS

This application claims the benefit of PCT/US2005/038140, filed Oct. 21, 2005, which claims the benefit of U.S. Provisional Application No. 60/625,397 filed Nov. 4, 2004, both of which are incorporated herein in their entirety.

BACKGROUND OF INVENTION

The morphinan alkaloids represent a family of structurally related natural products of great medicinal importance. An efficient total syntheses of the (−)-morphine and select derivatives has therefore been the objective of many synthetic efforts in the past century. Although a number of routes have been completed, all require long synthetic campaigns through numerous steps resulting in low overall yields and in some cases providing only racemic material. None are suitable for scale-up to a standard manufacturing process. Therefore, a practical method is needed that minimizes the number of steps and intermediate isolations, that is robust; that requires economical reagents and starting materials and that maximizes overall yield. To realize these goals, the methods disclosed in U.S. Pat. Nos. 4,368,326, 4,521,601 5,668,285 to Rice et al. (hereinafter Rice) and H. C. Beyerman, E. Buurman, L. Maat and C. Olieman, *Recl. Trav. Chim. Pays-Bas* 95, 184 (1976) (hereinafter Beyerman) have been used as basis for a hybrid synthesis into the morphinan ring system primarily focused on improving the key Grewe cyclization step.

Grewe cyclization is a ring closure method that in the present invention utilizes bromine or other halogens as a positional blocking group. The deactivating influence of halogen on the phenolic ring is overcome by the use of "super" acids in the Grewe cyclization (*J. Het. Chem.* June 1974, 363).

In the Beyerman synthesis, the key intermediate has an additional hydroxyl substitution on the aromatic ring that allows for Grewe cyclization under milder acid conditions, HCl/ethyl ether, but requires a subsequent dehydroxlation step to remove this activating function.

The Rice intermediates that undergo Grewe cyclization contain a methoxy, o-hydroxyl and m-bromo substitution pattern on the aromatic ring. Since these functions do not electron donate as much as three hydroxyls (Beyerman), a "super" acid medium, triflic acid, must be used to form the morphinan ring system. Any water contamination in the triflic acid greatly reduces the yield by the formation of a α,β-bicyclic-ketone and its polymerization by-products. Therefore, the Rice synthesis has a critical cyclization reaction in the middle of the route with very limited, severe, expensive acid requirements.

The dissolving metal reduction reaction well known in the art as the Birch reduction is used for reducing compounds, including the reduction of aromatic compounds to 1,3-cyclohexadiene or 1,4-cyclohexadiene and dehalogenation reactions. Although run under severe reaction conditions, the reduction is an important transformational tool for chemists and has been widely applied in organic synthesis in the partial reduction of an aromatic ring to 1,4-cyclohexadienes or 1,3-cyclohexadienes. Reduction of other functional groups on an aromatic ring or olefin, including the C—X bond, wherein X is a halogen, to C—H usually occurs.

The dissolving metal reduction comprises reacting with an alkali metal in the presence of a nitrogen containing base, usually ammonia. The alkali metal is typically Li, Na, K or Ca in a solvent system including simple alcohols and ethers held at reduced temperature.

The modified reduction reaction utilized in the present invention provides a method for preventing the reduction of at least one halogen substituted aromatic ring of an aromatic compound, while allowing the reduction of at least one functional group on the aromatic compound. This method is the subject of co-pending provisional application Ser. No. 60/534,592, filed Jan. 6, 2004, to the same assignee as the present invention. In this presently preferred method, at least one hydroxyl group and one halogen are substituted on the aromatic ring that does not undergo reduction. The aromatic compound is then reacted with at least one alkali metal in at least one nitrogen containing base and at least one alcohol, while maintaining a ratio of the alcohol to the nitrogen containing base. At least, one halogen substituted aromatic ring with a hydroxyl function is protected from reduction, while the desired group is reduced.

The reaction requires mild reaction conditions for the dissolving metal reduction. The modified metal reduction uses an alkali metal, typically lithium, sodium, potassium, calcium or a mixture thereof as a reductive reagent. The reaction further includes a nitrogen containing base, typically ammonia or a lower amine, and the presence of at least one alcohol. Suitable lower amines include but are not limited to ammonia, methylamine, ethylamine, ethylenediamine and mixtures thereof. The following solvent/nitrogen bases are particularly well suited for the present invention: a mixture of at least one alcohol and ammonia or at least one lower amine, or at least one alcohol, ammonia or at least one lower amine and at least one organic co-solvent. Suitable organic co-solvents include but are not limited to THF, ether and mixtures thereof. The dissolving metal reduction is carried out at a reduced temperature and at a ratio of nitrogen containing base to alcohol at which the reduction or dehalogenation of the protected aromatic ring is prevented. A presently preferred ratio of alcohol to nitrogen containing base is about 1:1 to about 1:4. The reaction temperature is typically maintained at about −30° C. or lower.

SUMMARY OF INVENTION

In one aspect of the present invention a method for the synthesis of an opiate intermediate is provided. The method comprises:

a) reacting a compound of Formula 1

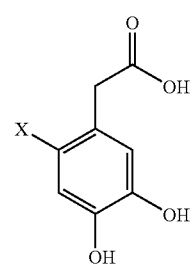

wherein X is F or Cl;

with at least one halide selected from the group consisting of sulfonyl halide and phosphorous halide to form a compound of Formula 2;

2

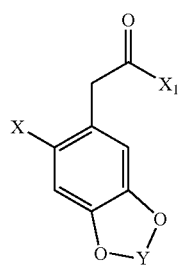

wherein X is a F or Cl; —X₁ is a Cl or Br; and wherein Y is SO when the halide is sulfonyl halide, and PCl when the halide is phosphorous halide;

b) reacting the compound of Formula 2 with a compound of Formula 3

3

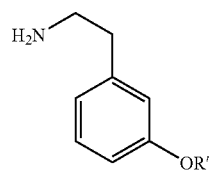

wherein R' is an alkyl, aryl or acyl group, in the presence of a base to form a compound of Formula 4;

4

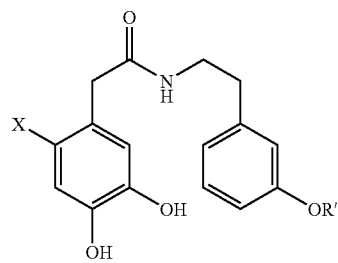

wherein X is a F or Cl; and R' is an alkyl, aryl or acyl group, c) reacting the compound of Formula 4 with at least one phosphoryl halide and then hydrolyzing to form a compound of Formula 5;

5

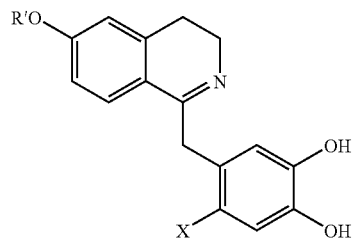

wherein X is a F or Cl; and R' is an alkyl, aryl or acyl group, d) reacting the compound of Formula 5 as a free imine or imine salt with a reducing agent to form a compound of Formula 6;

6

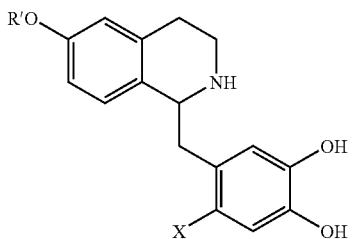

wherein X is a F or Cl and R' is an alkyl, aryl or acyl group, e) selectively reducing the compound of Formula 6 to form a compound of Formula 7;

7

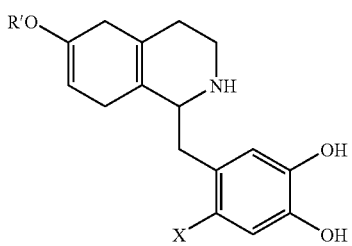

wherein X is a F or Cl and R' is an alkyl, aryl or acyl group, f) reacting the compound of Formula 7 with at least one formic acid ester, acyl halide, alkyl or aryl anhydride, alkyl haloformate, benzyl halide, alkyl halide or phenacylsulfonyl halide to form a compound of Formula 8;

8

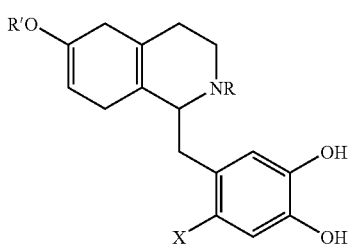

wherein X is a F or Cl; R' is an alkyl, aryl, or acyl and R is selected from the group consisting of formyl (CO), COR", COOR", Bn(benzyl), alkyl(methyl, ethyl, n-propyl, isopropyl, n-butyl, isobutyl, cyclopropylmethyl, cyclobutylmethyl, allyl, and etc.), and sulfonamide SO₂CH₂COPh, and wherein R" is selected from the group consisting of alkyl and aryl.

g) hydrolysis of the compound of Formula 8 forms a compound of Formula 9; and

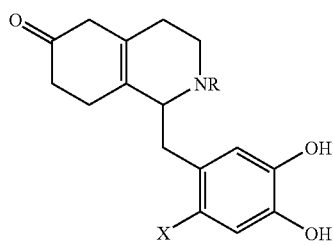

9

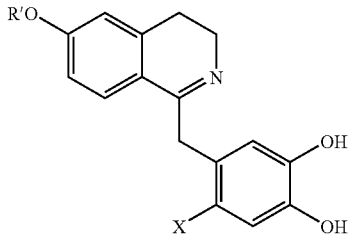

5 wherein X is a F and Cl and R' is an alkyl, aryl or acyl group;

wherein X is a F or Cl; and R is an H, alkyl, aryl, acyl, formyl, COR", COOR", Bn(benzyl), alkyl(methyl), and sulfonamide SO₂CH₂COPh.

h) converting the compound of Formula 9 under Grewe cyclization conditions in a strong acid to form the morphinan backbone, the compound of Formula 10.

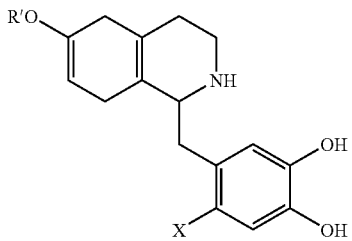

6 wherein X is a F or Cl and R' is an alkyl, aryl or acyl group;

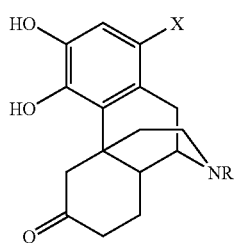

10

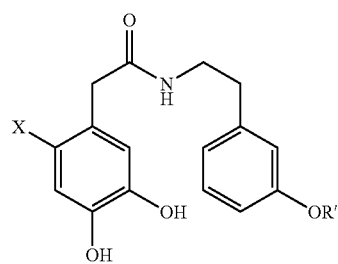

7 wherein X is a F or Cl and R is selected from the group consisting of formyl, COR", COOR", Bn(benzyl), alkyl(methyl), and sulfonamide SO₂CH₂COPh.

In another aspect of the present invention the following novel opiate synthesis intermediates are provided:

wherein X is a F or Cl and R' is an alkyl, aryl or acyl group;

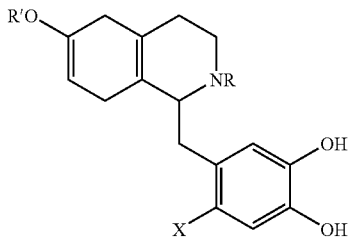

8

4 wherein X is a F or Cl and R' is an alkyl, aryl or acyl group;

wherein X is a F or Cl and R is an H, alkyl, aryl or acyl group; and

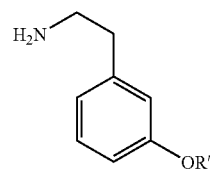

wherein X is a F or Cl and R is an H, alkyl, aryl or acyl group.

DETAILED DESCRIPTION

It has been determined that by changing the substitution pattern on the aromatic ring of the pre-Grewe intermediate from methoxy, o-hydroxyl and m-bromo (as disclosed by Rice) to dihydroxyl and m-halide (Cl or Br), the need for a "super" acid is obviated. Although the reaction still proceeds in triflic acid, much milder acids including but not limited to methanesulfonic acid, trifluoroacetic acid, sulfuric acid, phosphoric acid, p-toluenesulfonic acid, benzenesulfonic acid and boron trifluoride etherate can be used with much more tolerance to the presence of water. Further, the reaction is more robust and rearrangement to the α,β-bicyclic-ketone is minimized. Moreover, polymerization is mitigated. This route is also superior to that disclosed by Beyerman, since no dehydroxylation step required.

Therefore, there are provided novel opiate intermediates and an improved method for the synthesis of opiate intermediates. An embodiment of the present method comprises reacting a compound of Formula 1

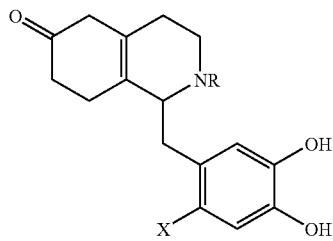

wherein X is a F or Cl;

with a sulfonyl halide or a phosphorous halide to form a compound of Formula 2. Suitable sulfonyl halides include $SOCl_2$ and $SOBr_2$ with $SOCl_2$ being preferred. Suitable phosphorous halides include $PBr_3$, $PCl_3$ and $PCl_5$. The halide reacts with the diol to form the heterocyclic ring of Formula 2. In an illustrative embodiment Formula 1 is heated to reflux in $SOCl_2$/toluene for about 3 hours, after which the solvent is removed by distillation.

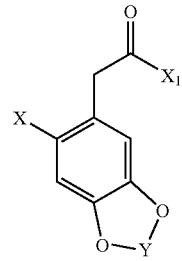

wherein Y is SO; X is F or Cl and $X_1$ is Cl or Br. In an embodiment where a phosphorous halide is utilized, Y would be PCl.

Formula 2 is then reacted with a compound of Formula 3 in the presence of a base to form a compound according to formula 4. Suitable bases include alkali bicarbonates, alkali carbonates, alkali phosphates (di- and tri-), ammonium hydroxide, ammonium acetate, organic buffers such as BICINE, TRICINE, TRIS, CAPS, CAPSO, EPPS, HEPES, MES, MOPS, PIPES, TAPS, TES or their sodium salts; organic bases like pyridine, triethylamine, diisopropylethylamine, N-methylmorpholine, N,N-dimethylaminopyridine or mixtures thereof. In an illustrative embodiment formula 2 is added to a mixture of $NaHCO_3/Na_3CO_3/NaHSO_3/H2O$ and Formula 3. After stirring the layers were separated to recover Formula 4 from the organic layer.

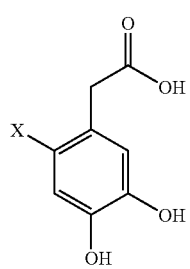

wherein R' is an alkyl, aryl or acyl group

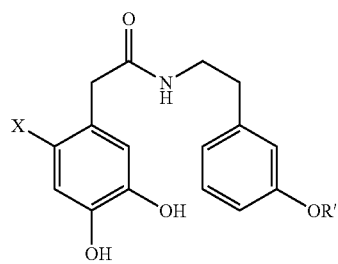

The compound of Formula 4 is then treated with at least one phosphoryl halide followed by hydrolysis to form a compound according to Formula 5. Suitable phosphoryl halides include $POCl_3$ and $POBr_3$, with $POCl_3$ being preferred. Suitable methods of hydrolysis include aqueous reflux at adjusted pH. Typical bases utilized to adjust the pH to a desired range include alkali carbonates, alkali phosphates, sodium hydroxide, sodium acetate, ammonium acetate or ammonium hydroxide. In an illustrative embodiment, the compound of Formula 4 heated to a temperature in $POCl_3$/acetonitrile at which it completely dissolves is taken to reflux. An oily product is recovered, re-dissolved in acetonitrile, pH adjusted to 4-5 and refluxed. Formula 5 is produced as a crystalline solid.

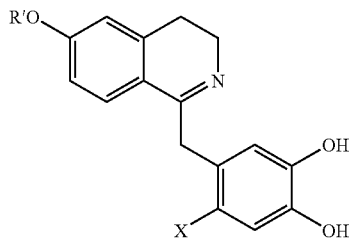

5

Formula 5 as a free imine is then reduced to form Formula 6. Suitable reduction reactions include NaBH$_4$, NaCNBH$_3$, H$_2$ and Pt, Pd, Ir, Ru or Rh on Carbon in a solvent such as ethanol, methanol, isopropanol, propanol, formic, formate salt and acid, THF, ethyl acetate, and mixtures thereof. In an alternative embodiment of the present invention, chiral organometallic catalysts (Ru, Rh, Ir, Pt, Pd, . . . bearing chiral ligands) or chiral hydrides may be used to induce the enantiomeric center at the benzylic position adjacent to the nitrogen. In the chiral case, for example, sodium triacyloxyborohydride generated from N-benzyloxycarbonylproline and borohydrides has been used to prepare similar enantiomeric tetrahydroquinolines from the corresponding imines. (For illustrative examples consult pages 230-240 of "Chiral Auxiliaries and Ligands in Asymmetric Synthesis" by Jacqueline Seyden-Penne, John Wiley & Sons publisher, NY, 1995) In an illustrative embodiment of reduction to the racemate, the compound of Formula 5 is refluxed in ethanol, after which NaBH$_4$ is added.

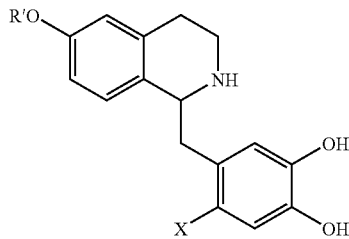

6

Formula 6 is then selectively reduced to form a compound of Formula 7. The reaction requires mild reaction conditions for the dissolving metal reduction. The modified metal reduction uses an alkali metal, typically lithium, sodium, potassium, calcium or a mixture thereof as a reductive reagent. The reaction further includes a nitrogen containing base, typically ammonia or a lower amine, and the presence of at least one alcohol. Suitable lower amines include but are not limited to ammonia, methylamine, ethylamine and mixtures thereof. The following solvent/nitrogen bases are particularly well suited for the present invention: a mixture of at least one alcohol and ammonia or at least one lower amine, or at least one alcohol, ammonia or at least one lower amine and at least one organic co-solvent. Suitable organic co-solvents include but are not limited to THF, ether and mixtures thereof. The dissolving metal reduction is carried out at a reduced temperature and at a ratio of nitrogen containing base to alcohol at which the reduction or dehalogenation of the protected aromatic ring is prevented. A presently preferred ratio of alcohol to nitrogen containing base is about 1:1 to about 1:4. The reaction temperature is typically maintained at about −30° C. or lower.

In an illustrative embodiment formula 6 is suspended in ethanol/ammonia and cooled to about −70 C under nitrogen. NaOEt is added, followed by cut sodium metal. Upon completion, the reaction mixture is allowed to warm, the reaction is quenched and a suspension of compound of Formula 7 is recovered.

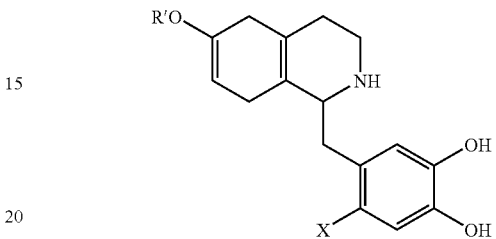

7

Formula 7 is reacted with at least one formic acid ester to form Formula 8. Suitable formic acid esters include HCO$_2$Pr, HCO$_2$Et, HCO$_2$Bn, HCO$_2$Me, HCO$_2$nBu, HCO$_2$Ph and mixtures thereof. In an illustrative embodiment, Formula 8 is suspended in HCO$_2$Pr and heated to reflux. After the solvent is removed, a powder residue comprised of the compound of Formula 8 remains. Optionally, the compound of Formula 8 may be used in the subsequent process step.

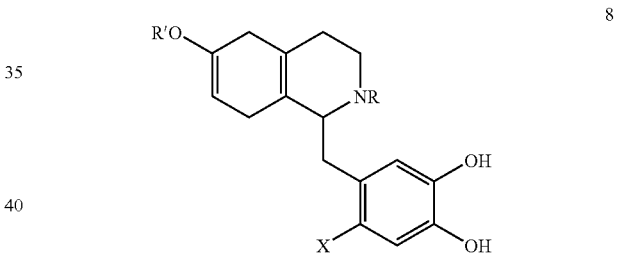

8

Formula 8 is hydrolyzed to form a compound of Formula 9. Suitable hydrolysis reactions include aqueous acetic acid, or other aqueous acids at a controlled pH, as are well known in the art. In an illustrative embodiment, Formula 8 is mixed with formic acid and the compound of Formula 9 is then extracted with ethyl acetate.

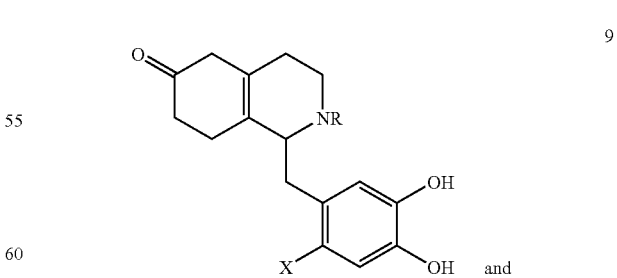

9 and

Formula 9 is then converted to formula 10 under Grewe cyclization conditions. The Grewe method is an acid catalyzed ring closure of a substituted tetrahydroisoquinoline to the corresponding morphinan ring system, as is well known in the art. Suitable acid medium include but are not limited to methanesulfonic acid, p-toluenesulfonic acid, benzenesulfonic acid, sulfuric acid, trifluoroacetic acid, trifluoromethanesulfonic acid, phosphoric acid and mixtures thereof. Optionally, the acidic media may consist of a Lewis acid in solution such as boron trifluoride etherate. In an illustrative embodiment formula 9 is dissolved in CHCl$_3$ and added to the acidic medium chosen from the group including but not limited to methanesulfonic acid, p-toluenesulfonic acid, benzenesulfonic acid, sulfuric acid, trifluoroacetic acid, trifluoromethanesulfonic acid, phosphoric acid and mixtures thereof

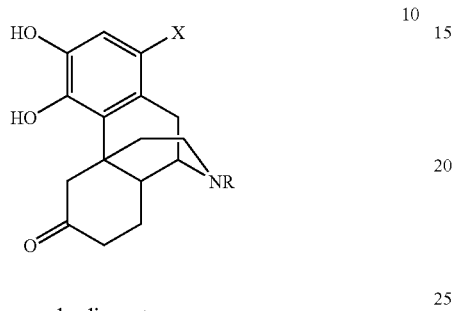

10

In an alternative embodiment

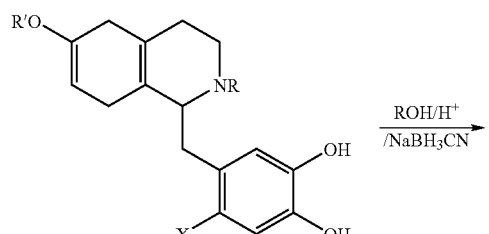

8

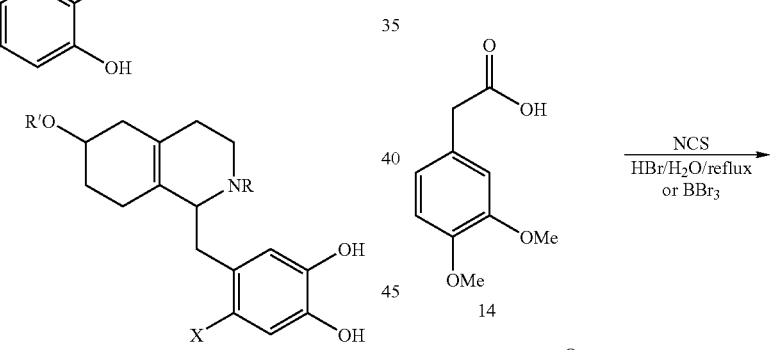

11 wherein X is a halogen and R is H, alkyl, acyl, aryl or R is selected from the group consisting of formyl, COR″, COOR″, Bn(benzyl), alkyl(methyl), and sulfonamide SO$_2$CH$_2$COPh.

In yet another alternative embodiment

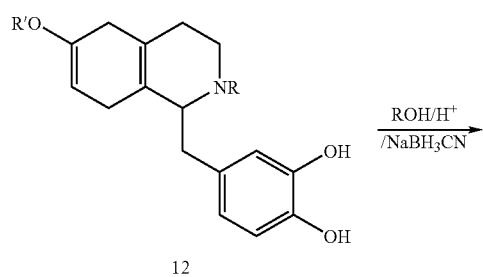

12

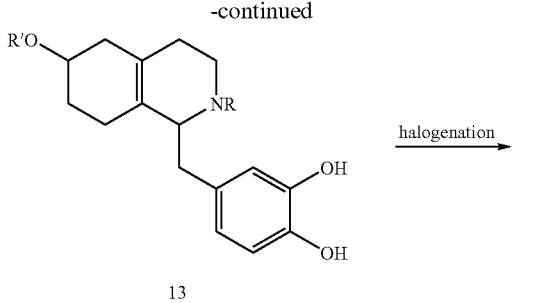

13

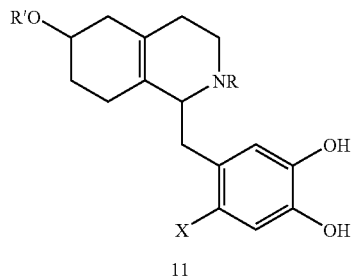

11 wherein X is a halogen and R is H, alkyl, acyl, aryl, formyl, COR″, COOR″, Bn(benzyl), alkyl(methyl), and sulfonamide SO$_2$CH$_2$COPh.

A non-limiting illustrative example of the reaction scheme of the present invention follows. The reactions are explained in detail in the examples that follow.

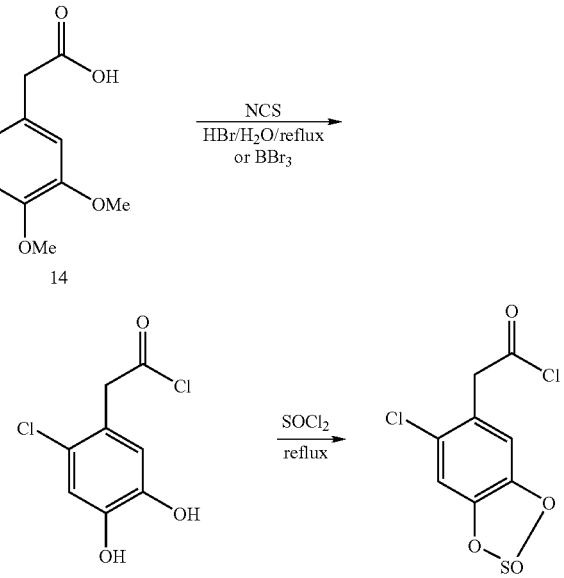

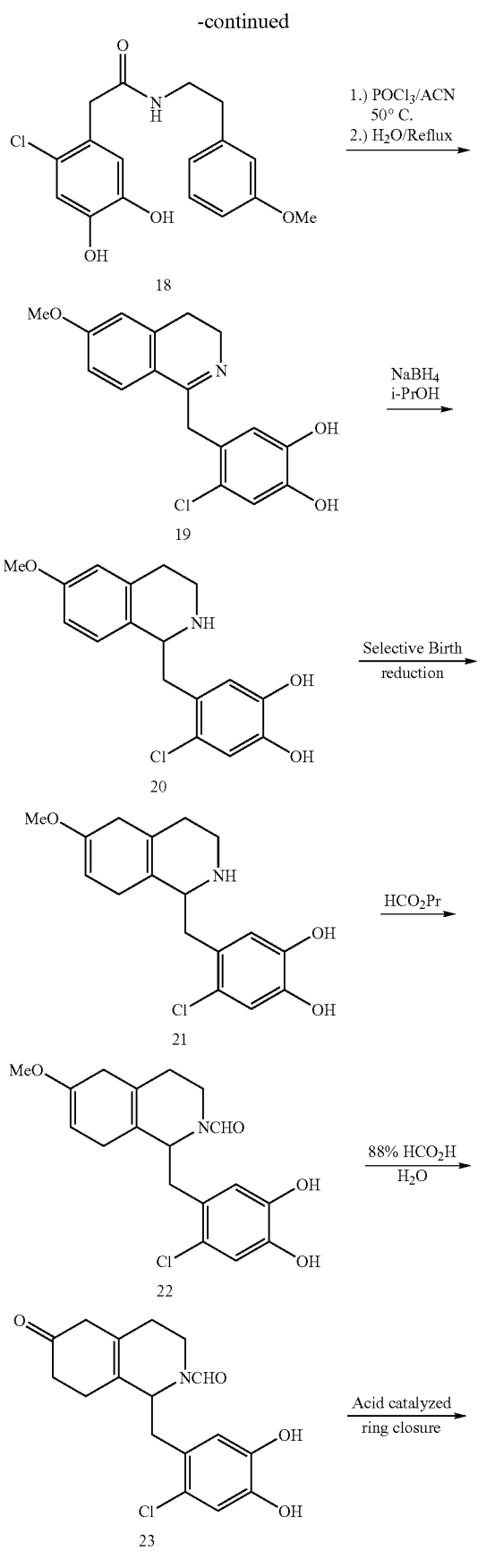

The following novel compounds are illustrative of the types of compounds that can be synthesized by the instant method. These compounds are in no way all inclusive or limiting of the present invention.

Formula 20

4-chloro-5-((1,2,3,4,5,8-hexahydro-6-methoxyisoquinolin-1-yl)methyl)benzene-1,2-diol 4-chloro-5-(((R)-1,2,3,4,5,8-hexahydro-6-methoxyisoquinolin-1-yl)methyl)benzene-1,2-diol 4-chloro-5-(((S)-1,2,3,4,5,8-hexahydro-6-methoxyisoquinolin-1-yl)methyl)benzene-1,2-diol Formula 27

1-(2-fluoro-4,5-dihydroxybenzyl)-3,4-dihydro-6-methoxyisoquinoline-2(1H,5H,8H)-carbaldehyde

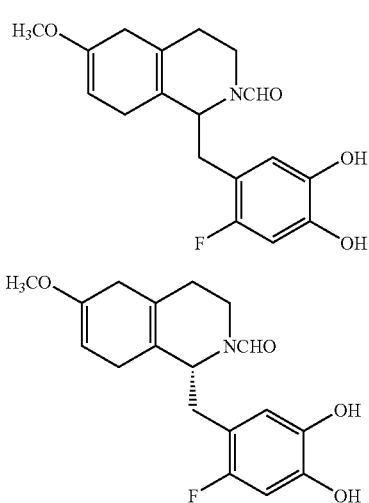

(R)-1-(2-fluoro-4,5-dihydroxybenzyl)-3,4-dihydro-6-methoxyisoquinoline-2(1H,5H,8H)-carbaldehyde

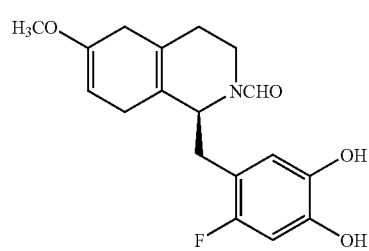

(S)-1-(2-fluoro-4,5-dihydroxybenzyl)-3,4-dihydro-6-methoxyisoquinoline-2(1H,5H,8H)-carbaldehyde Formula 28
4-fluoro-5-((1,2,3,4,5,8-hexahydro-6-methoxyisoquinolin-1-yl)methyl)benzene-1,2-diol

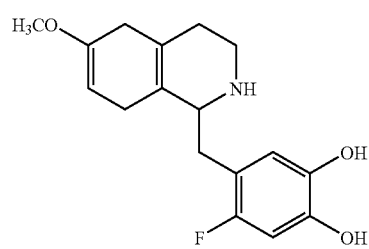

4-fluoro-5-(((R)-1,2,3,4,5,8-hexahydro-6-methoxyisoquinolin-1-yl)methyl)benzene-1,2-diol

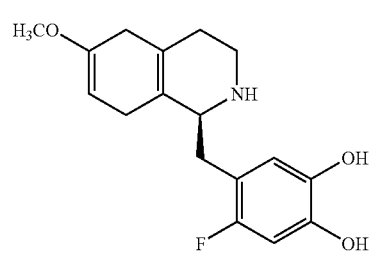

4-fluoro-5-(((S)-1,2,3,4,5,8-hexahydro-6-methoxyisoquinolin-1-yl)methyl)benzene-1,2-diol Formula 29
1-(2-chloro-4,5-dihydroxybenzyl)-1,2,3,4,7,8-hexahydroisoquinolin-6(5H)-one

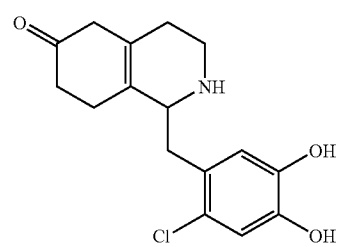

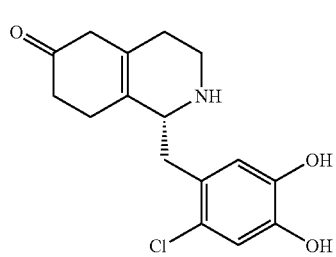

(R)-1-(2-chloro-4,5-dihydroxybenzyl)-1,2,3,4,7,8-hexahydroisoquinolin-6(5H)-one

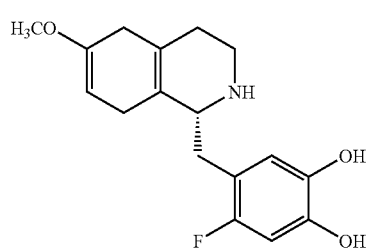

(S)-1-(2-chloro-4,5-dihydroxybenzyl)-1,2,3,4,7,8-hexahydroisoquinolin-6(5H)-one

Formula 30
1-(2-chloro-4,5-dihydroxybenzyl)-3,4,6,7,8,8a-hexahydro-6-oxoisoquinoline-2(1H)-carbaldehyde

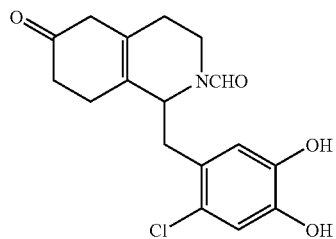

30

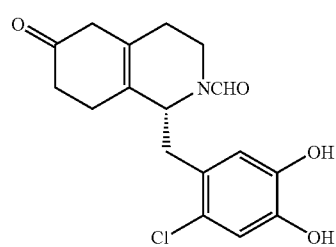

30R (R)-1-(2-chloro-4,5-dihydroxybenzyl)-3,4,5,6,7,8-hexahydro-6-oxoisoquinoline-2(H)-carbaldehyde

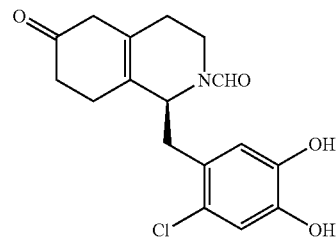

30S (S)-1-(2-chloro-4,5-dihydroxybenzyl)-3,4,5,6,7,8-hexahydro-6-oxoisoquinoline-2(1H)-carbaldehyde Formula 31
1-(2-chloro-4,5-dihydroxybenzyl)-1,4,4a,5,6,8a-hexahydro-6-oxoisoquinoline-2(3H)-carbaldehyde

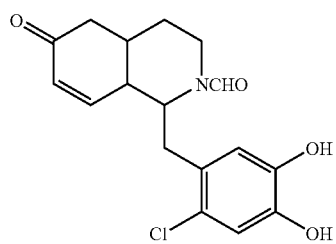

31

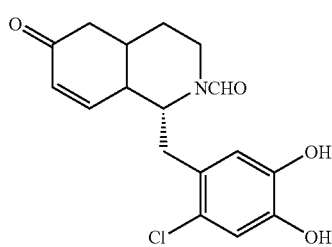

31R (1R)-1-(2-chloro-4,5-dihydroxybenzyl)-1,4,4a,5,6,8a-hexahydro-6-oxoisoquinoline-2(3H)-carbaldehyde

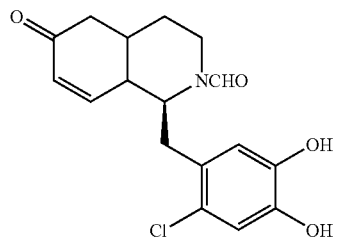

31S (1S)-1-(2-chloro-4,5-dihydroxybenzyl)-1,4,4a,5,6,8a-hexahydro-6-oxoisoquinoline-2(3H)-carbaldehyde Formula 32
1-(2-chloro-4,5-dihydroxybenzyl)-1,2,3,4,4a,5-hexahydroisoquinolin-6(8ah)-one

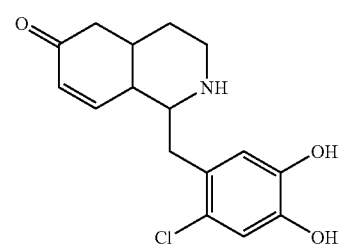

32

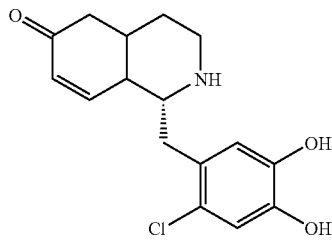

32R (1R)-1-(2-chloro-4,5-dihydroxybenzyl)-1,2,3,4,4a,5-hexahydroisoquinolin-6(8aH)-one

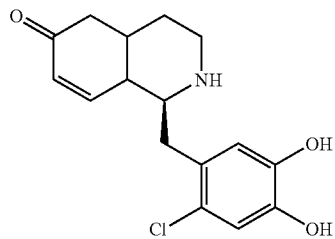

(1S)-1-(2-chloro-4,5-dihydroxybenzyl)-1,2,3,4,4a,5-hexahydroisoquinolin-6(8aH)-one
Formula 33
1-(2-chloro-4,5-dihydroxybenzyl)-1,2,3,4,8,8a-hexahydroisoquinolin-6(7H)-one

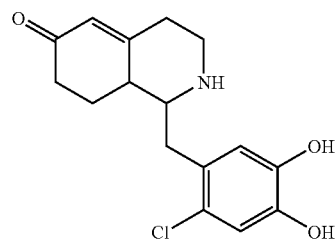

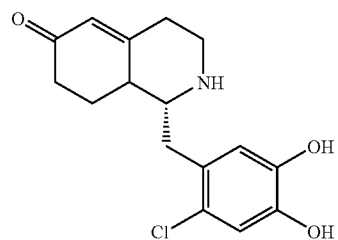

(1R)-1-(2-chloro-4,5-dihydroxybenzyl)-1,2,3,4,8,8a-hexahydroisoquinolin-6(7H)-one

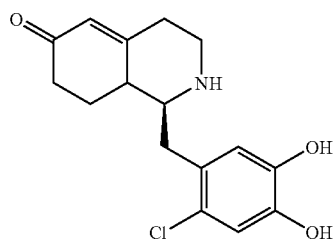

(1S)-1-(2-chloro-4,5-dihydroxybenzyl)-1,2,3,4,8,8a-hexahydroisoquinolin-6(7H)-one As with the scheme and compounds given above, the examples herein are provided for purposes of illustration only and are not intended in any way to be limiting of the present invention.

EXAMPLES

Example 1

Chlorination of Formula 14

Formula 14 (238.0 g, 1.21 mol) when added to THF/c-HCl (1250 mL/125 mL) formed a yellow solution. The solution was cooled down to −10° C. in a dry-ice/i-PrOH bath. N-chlorosuccimide (NCS) (170.0 g, 1.05 eq) was added in five portions over a 2 h period. Water (1200 mL) was then added. Solvent (~1500 mL) was distilled off until distillate vapor temperature reached 100° C. The mixture with stirring was allowed to cool down overnight to give crystals. It was filtered. The filtrate (1250 mL) was obtained and HPLC analysis indicated that it contained 5 grams of product. The solid washed with water (200 mL, 150 mL×2) and dried in flowing air for 4 hours to give 326.8 g of wet solid of pure product by HPLC analysis.

Example 2

Preparation of Formula 15

The crude product of Example 1 was suspended in 48% HBr and heated to 90° C. for form a brown solution. It was stirred at 90° C. for 6 h, heated at 100° C. for 3 h and then cooled to room temperature. The suspension was left stirring over the weekend. The mixture was filtered and the recovered solid washed with water (600 mL). The solid was dried in flowing air for 4 h to give 256 g of solid. It was dissolved in refluxing ethyl acetate (1000 mL). 100 grams of activated carbon was added. The mixture was refluxed for another 10 minutes and filtered hot. The filter washed with hot ethyl acetate (250 mL×2). The combined organic solutions were taken to dryness under vacuum, and the product (156.05 g) was recovered as off white solid.

Example 3

Preparation of Formula 15

To a solution of the dried product of Example 1 (55.0 g, 0.238 mol) in CH$_2$Cl$_2$ (500 mL) at 10° C., BBr$_3$ (50 mL, 2.2 eq) was added. The mixture was stirred for 30 minutes after the addition was completed and then poured into water (1000 mL), it was heated to reflux for 1 hour. Dichloromethane was removed by distillation until the distillate vapor temperature reached 100° C. The remaining solution was allowed to cool down and then extracted with ethyl acetate (300 mL, 150 mL×2). The combined organic layers were washed with water (300 mL×2) and taked to dryness under vacuum to give 41.5 g of product as solid.

Example 4

Preparation of Formula 18

The compound of Example 3 (38.4 g, 0.19 mol) was heated to reflux in SOCl$_2$/toluene (120 mL/300 mL for 3 hours. 260 Milliliters of solvent were distilled off under reduced pressure at 60° C. The solution was cooled down to room temperature.

It was added to a mixture of NaHCO$_3$/NaHSO$_3$/H$_2$O (80 g/15 g/800 mL) and ethyl acetate (35 g of 17/400 mL) over 20 minutes. The mixture was stirred for another 30 minutes after the addition and then the layers were separated. The aqueous layer was extracted with ethyl acetate (400 mL). The combined organic layers were washed with NaHCO$_3$/NaHSO$_3$/H$_2$O (80 g/15 g/800 mL), 400 mL×2. The organic layers were washed in 1N HCl (500 mL, 250 mL×2). The solvent was removed under reduced pressure affording the product as a sticky oil, 56.2 g.

Example 5

Preparation of Formula 19

The compound of Example 4 (56.2 g) was dissolved in POCl$_3$/ACN (50 mL/250 mL) at 50° C. for 1 hour and then refluxed for 1 hour. The solution was taken to dryness under vacuum. It was re-dissolved in ACN (350 mL) and poured into water (500 mL). The mixture was heated to reflux and the pH was adjusted to 3-4. The heating at reflux was continued for 18 hours. 350 mL solvent was removed by distillation. The solution was cooled to 80° C. ACN (50 mL) was added and further cooling of the solution to 10° C. provided crystals. The crystals were separated by filtration. The solid washed with water (100 mL×2, 50 mL) and dried under an air flow overnight to give 44.2 g of solid.

Example 6

Chlorination of the Compound of Formula 14

The compound of Formula 14 (229.0 g, 1.17 mol) was added to THF/c-HCL (1000 mL/100 mL) forming a yellow solution. It was cooled to 5-10° C. over ice bath. N-Chlorosuccinimide (NCS, 164.0 g, 1.05 eq) was added in four portions over 1 hour. The mixture was stirred and maintained at about 10° C.-20° C. during and for 30 minutes following the addition. The mixture was allowed to warm to RT with stirring over another 30 minutes. Water (1000 mL) was added. THF was removed by distillation until the distillate vapor temperature reached 100° C. The remaining liquid was allowed to cool to 5° C. with stirring over 2 hours. The crystals formed on cooling were filtered. The solid washed with water (200 mL, 150 mL×2) and dried in flowing air for 18 hours to give 266.3 g.

Example 7

Preparation of Formula 15

The crude product yield of Example 6 (265 g) was suspended in 48% HBr (1000 mL) and heated at 95° C. for 1 hour and then taken to reflux for 3 hours. A crystalline solid formed on cooling to 5° C. The crystals were separated by filtration. The crystals were washed with water (200 mL, 150 mL) and dried under house vacuum at 70° C. for 3 hours to give 158.5 g of product.

Example 8

Preparation of Formula 18

The compound of Example 7 (10.1 g, 50.0 mmol) was heated to reflux in SOCl$_2$/toluene (10.9 mL/100 mL) for 3 hours. The solvent (50 mL) mainly SOCl$_2$ was removed by distillation. The reaction mixture was cooled to 25° C. and added to a mixture of NaHCO$_3$/Na$_3$CO$_3$/NaHSO$_3$/H$_2$O (16.8 g/10.6 g/2.6 g/200 mL) and ethyl acetate (9.1 g 17/100 mL) over 20 minutes. The mixture was set aside with stirring for 30 minutes after the addition. The phases were separated, and the aqueous layer was extracted with ethyl acetate (50 mL×2). The combined organic layers were washed with 100 mL of NaHCO$_3$/NaHSO$_3$/H$_2$O (15 g/3 g/150 mL) and then 50 mL×3. The organic layer was washed with 1 N HCl (100 mL, 50 mL×2). The solvent was removed under reduced pressure to give sticky solid, 15.2 g.

Example 9

Preparation of Formula 18

The compound of Example 7 (101.3 g, 0.5 mmol) was heated to reflux in SOCl$_2$/toluene (109 mL/1000 mL) for 3 hours. Solvent (500 mL) was removed by distillation. The remaining solution was cooled to 25° C. and added to a mixture of NaHCO$_3$/Na$_3$CO$_3$/NaHSO$_3$/H$_2$O (168 g/106 g/26 g/1500 mL) and ethyl acetate (91 g of 17/800 mL) over 20 minutes. The mixture was set aside with stirring for 30 minutes after the addition. The phases were separated, and the aqueous layer was extracted with ethyl acetate (700 mL). The combined organic layers were washed with NaHCO$_3$/NaHSO$_3$/H$_2$O (50 g/3 g/700 mL) and then 400 mL×2. The organic layer washed with 1 N HCl (700 mL, 400 mL×2). The solvent was removed under reduced pressure to give a sticky solid, 150.4 g.

Example 10

Preparation of Formula 19

The compound of Example 9 (150 g) was dissolved in POCl$_3$/ACN (163 mL/750 mL) at 50 C for 1 hour and then refluxed for 1 hour. An oily material was recovered after the volatiles were removed under reduced pressure. The oil was re-dissolved in ACN (750 mL) and poured into water (1500 mL). The mixture was heated to reflux and the pH was adjusted to 4-5. Heating at reflux was continued for 22 hours. Once the solvent (850 mL) had been removed by distillation, the solution was cooled down to 80° C. After the ACN (150 mL) was added, the solution was allowed to cool to 10° C. to give crystals. The crystals were separated by filtration. The solid washed with water (500 mL×2) and was dired under a flow of air overnight to give 131.5 g product as a solid.

Example 11

Preparation of Formula 20

The compound formed in Example 10 (100.0 g) was refluxed in EtOH (1000 mL). NaBH$_4$ (21.1 g) was added in portions. Hydrogen was released during the addition but stopped 10 minutes post addition. The suspension was heated to reflux for 30 minutes. Water (1500 mL) was added slowly and conc. HCl (~75 mL) was added until pH is 0-1. Solvent (1500 mL) was removed by distillation until the distillate temperature reached 99° C. After a solid began to form the mixture was allowed to cool to RT. After 3 hours the solids were separated by filtration. The solid washed with water (100 mL×3) and dried under a flow of air for 1 hour to give 173 g wet solid H$_3$PO4 salt product.

The wet product (172 g) was dissolved in HCl (1N, 500 mL)/EtOH (500 mL) under reflux. The hot solution was added into a mixture of NH$_4$OH (29.4%, 80 mL)/H$_2$O (400 mL)/ice (1000 g) with stirring to give a precipitate. The mixture was stirred for an additional hour. The solids were separated by filtration. The material washed with water (200 mL, 200 mL×3) and dried under a flow of air overnight to give 82.1 g.

Example 12

Preparation of Formula 21

The compound of Example 11 (28 g) was suspended in EtOH (750 mL) and cooled to −70° C. Ammonia ($NH_3$) was condensed into the EtOH to a final volume of 1500 mL at −70° C. The solution was kept under a flow of nitrogen. NaOEt (25.2 g) was added and stirred for 10 minutes. Cut sodium metal was added to the mixture at −55° C. to about −70° C. in five portions. The reaction is monitored by HPLC analysis to follow the course of the Birch reduction. A total of 4.80 g sodium was necessary for completion of the reaction. After stirring another 30 min., the mixture was allowed to warm to 0-10° C. The ammonia evaporated on warming. The reaction was quenched with $HCO_2H/H_2O$ and $NH_4Cl/H_2O$ to pH 6 to 8 and then diluted to a total volume of 2000 mL with water. The suspension was stirred for 30 minutes and filtered. The solid obtained washed with water (150 mL×4) and was dried under a flow of air overnight to give the product as powder, 25.3 g.

Example 13

Preparation of Formula 22

The compound of Example 8 (24 g) was suspended in $HCO_2Pr$ (850 mL) and heated to reflux for 3 hours. The solvent (550 mL) was removed by distillation. The remaining suspension with stirring was allowed to cool to RT over a 30 minute period. The solids were separated by filtration and then washed with ether (50 mL×4) followed by hexane (50 mL×2). After drying under an air flow for 2 hours, the product remained as a powder, 21.3 g. Another 3.63 g of product was recovered by removing the volatiles under vacuum from the combined filtrates and washes.

Example 14

Preparation of Formula 23

The compound of Example 13 (1.0 g) was stirred in 88% $HCO_2H/H_2O$ (12 mL) for 30 minutes to form a brown solution. The solution was diluted further with water (50 mL) and extracted with ethyl acetate (25 mL×2). The combined organic layers were washed with water (25 mL×3) and the volatile components removed under vacuum. The remaining solid was redissolved in ethyl acetate followed y removal of the solvent under reduced pressure to afford 0.80 g of product as a solid.

Example 15

Preparation of Formula 24

The pre-cyclized intermediate of Example 14 (1.00 g) was dissolved in $CHCl_3$ (20 mL) and added over 15 minutes to trifluoromethanesulfonic acid (5 mL) cooled to about −40° C. to −20° C. This reaction mixture was allowed to warm to RT and stir overnight. The mixture was diluted with 200 mL $H_2O$ and 200 mL ethyl acetate. $NH_4OH$ (28%) was added to adjust pH to 8.5 and stirred for 2 hours. $HCO_2H$ was added until pH was 4. After stirring for 0.5 hour, the phases were separated. The water layer was extracted with ethyl acetate (100 mL). The combined organic layers were washed with 0.01 N HCl (200 mL×3) dried over $K_2SO_4$ and filtered. After the solvents were removed under reduced pressure, 1.05 g of solid remained. The product was isolated from the mixture by HPLC.

Example 16

Preparation of Formula 27

Formula 27 was prepared according to Example 13 with F as the halogen.

Example 17

Preparation of Formula 28

Formula 28 was prepared according to Example 12, with F as the halogen.

Example 18

Preparation of Formula 29

Formula 29 is prepared according to Example 14, substituting the N-formyl group with a free amino group for the compound of Example 13.

Example 19

Preparation of Formula 30

The compound of Example 13 (0.50 g) was dissolved in $MeSO_3H$ (5 mL) and allowed to stand for 2.5 h before addition to a solution of $NH_4OH$ in MeOH (100 mL). The pH was adjusted to 4. The mixture was diluted with water (100 mL) and extracted with ethyl acetate (2×100 mL). The combined organic layers were washed with $NaH_2PO_4$ solution (2×100 mL), dried over $Na_2SO_4$ and filtered. The filtered solution was placed under vacuum to remove the volatile solvents. 0.52 Gram of solid crude product remained. HPLC analysis of the crude indicated that the solid contained 90% α,β-ketone, Formula 30.

Example 20

Preparation of Formula 31

Formula 31 is a byproduct of the acid-catalyzed rearrangement of compound formed in Example 19.

Example 21

Preparation of Formula 32

Formula 32 is a byproduct of the acid-catalyzed rearrangement of the compound formed in Example 18.

Example 22

Preparation of Formula 33

Formula 33 is prepared according to Example 19, substituting the compound of Formula 29 for the compound of Formula 23.

The invention claimed is:

1. A method comprising reacting a compound of Formula 12 with at least one reducing agent in a solvent including at least one alcohol to form a compound of Formula 13, and halogenating the compound of Formula 13 to form a compound of Formula 11:

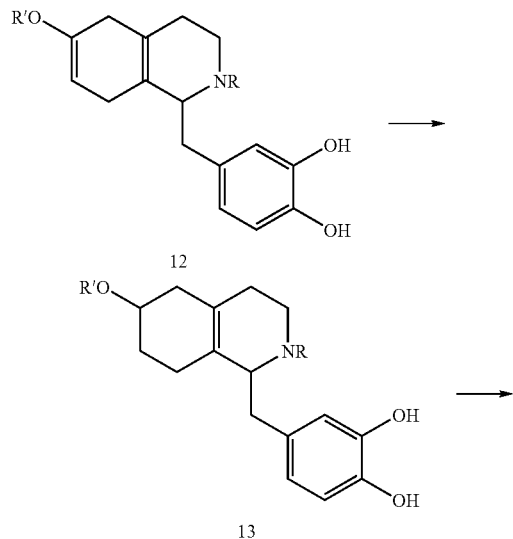

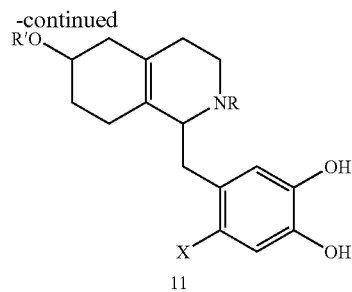

wherein:
X is a halogen;
R is H, alkyl, acyl, aryl, formyl, COR", COOR", benzyl, or sulfonamide;
R' is alkyl, aryl or acyl; and, R" is alkyl or aryl.

2. The method of claim 1 wherein the reducing agent is selected from $NaBH_4$, $NaBH_3CN$, $H_2$ and Pt, Pd, Ir, Ru or Rh on Carbon and wherein the solvent includes at least one solvent selected from the group consisting of ethanol, methanol, isopropanol, propanol, formic a cid, formate salt, THF, ethyl acetate and mixtures thereof.

3. The method of claim 1 wherein R is selected from the group consisting of methyl, ethyl, n-propyl, isopropyl, n-butyl, isobutyl, cyclopropylmethyl, and cyclobutylmethyl.

* * * * *